US00PP18411P2

(12) United States Plant Patent
Andrusiv

(10) Patent No.: US PP18,411 P2
(45) Date of Patent: Jan. 8, 2008

(54) ***BERBERIS* PLANT NAMED 'ORANGE ROCKET'**

(50) Latin Name: *Berberis thunbergii*
Varietal Denomination: Orange Rocket

(76) Inventor: Michal Andrusiv, J Metyse 1079, Litomyal (CZ), 570 01

( * ) Notice: Subject to any disclaimer, the term of this patent is extended or adjusted under 35 U.S.C. 154(b) by 1 day.

(21) Appl. No.: 11/544,376

(22) Filed: Oct. 10, 2006

(51) Int. Cl.
*A01H 5/00* (2006.01)

(52) U.S. Cl. ..... Plt./241
(58) Field of Classification Search ..... Plt./241
See application file for complete search history.

*Primary Examiner*—Kent Bell

(57) ABSTRACT

A new cultivar of *Berberis* plant named 'ORANGE ROCKET' that is characterized by an upright columnar habit and rust-orange colored foliage. In combination these traits set 'ORANGE ROCKET' apart from all other existing varieties of *Berberis* known to the inventor.

1 Drawing Sheet

Genus: *Berberis*. Species: *thunbergii*.
Denomination: 'ORANGE ROCKET'.

BACKGROUND OF THE INVENTION

The present invention relates to a new and distinct cultivar of barberry that is grown as a dwarf shrub for container or landscape. The new cultivar is known botanically as *Berberis thunbergii* and will be referred to hereinafter by the cultivar name 'ORANGE ROCKET'.

'ORANGE ROCKET' was selected by the inventor in Litomysl, The Czech Republic in 1994, for unique foliage color. The new cultivar 'ORANGE ROCKET' is a hybrid plant that resulted from cross-pollination conducted by the inventor in a cultivated area of Litomysl, The Czech Republic. Cross-pollination was between an individual plant of seed parent *Berberis thunbergii* 'Aurea' (unpatented) and an individual plant of pollen parent *Berberis thunbergii* 'Helmond Pillar' (unpatented).

The new *Berberis* variety 'ORANGE ROCKET' is a deciduous dwarf shrub characterized by rust-colored foliage. This foliage color continues throughout the summer season. The height of the plant is three times its width. The foliage color and plant habit distinguish 'ORANGE ROCKET' from all other *Berberis* known to the inventor.

The new *Berberis* variety 'ORANGE ROCKET' differs from the yellow foliaged female parent plant *Berberis thunbergii* 'Aurea' in that 'ORANGE ROCKET' is columnar. The new *Berberis* variety 'ORANGE ROCKET' differs from the purple foliaged male parent plant *Berberis thunbergii* 'Helmond Pillar' in that 'ORANGE ROCKET' is rusty orange in color and slightly smaller in size. The closest known varieties of *Berberis thunbergii* known to the inventor are the two parental cultivars described above.

The first asexual reproduction of 'ORANGE ROCKET' was conducted by the inventor in 1995 in a cultivated area of Litomysl, The Czech Republic. The method used for asexual propagation was vegetative cuttings. Since that time the distinguishing characteristics of 'ORANGE ROCKET' have been determined stable and have reproduced true to type in successive generations of asexual reproduction.

SUMMARY OF THE INVENTION

The following traits have been repeatedly observed and represent the characteristics of the new *Berberis* cultivar 'ORANGE ROCKET'. These traits in combination distinguish 'ORANGE ROCKET' from all other commercial varieties of *Berberis* known to the inventor. 'ORANGE ROCKET' has not been tested under all possible conditions and phenotypic differences may be observed with variations in environmental, climatic and cultural conditions, without however, any variance in genotype.

1. *Berberis* 'ORANGE ROCKET' is a deciduous shrub.
2. *Berberis* 'ORANGE ROCKET' is suitable for use in containers or the landscape.
3. *Berberis* 'ORANGE ROCKET' exhibits an upright, columnar habit.
4. *Berberis* 'ORANGE ROCKET' exhibits rust-orange colored foliage.
5. *Berberis* 'ORANGE ROCKET' is propagated using vegetative cuttings.
6. *Berberis* 'ORANGE ROCKET' is hardy to USDA Zone 5.
7. After 10 years, *Berberis* 'ORANGE ROCKET' achieves 120 cm in height and 40 cm in width.

BRIEF DESCRIPTION OF THE DRAWING

The accompanying color drawing, FIG. 1, illustrates the overall appearance of the new cultivar 'ORANGE ROCKET' showing the colors as true as it is reasonably possible to obtain in colored reproductions of this type. The plant shown in the drawing is 2-years-old grown out-of-doors in Boskoop, The Netherlands. The specimen is in the center against a background of golden-green foliaged shrubs. The drawing illustrates the rusty orange foliage and upright habit of 'ORANGE ROCKET'. Daytime temperatures averaged 15° Centigrade to 30° Centigrade. Nighttime temperatures ranged from −7° Centigrade to 14° Centigrade. The light was normal outdoor light level. No photoperiodic treatments and no growth retardants were applied to the plants. Colors in the drawing may differ from the color values cited in the detailed botanical description, which accurately describe the actual colors of the new variety of

Figure 1:
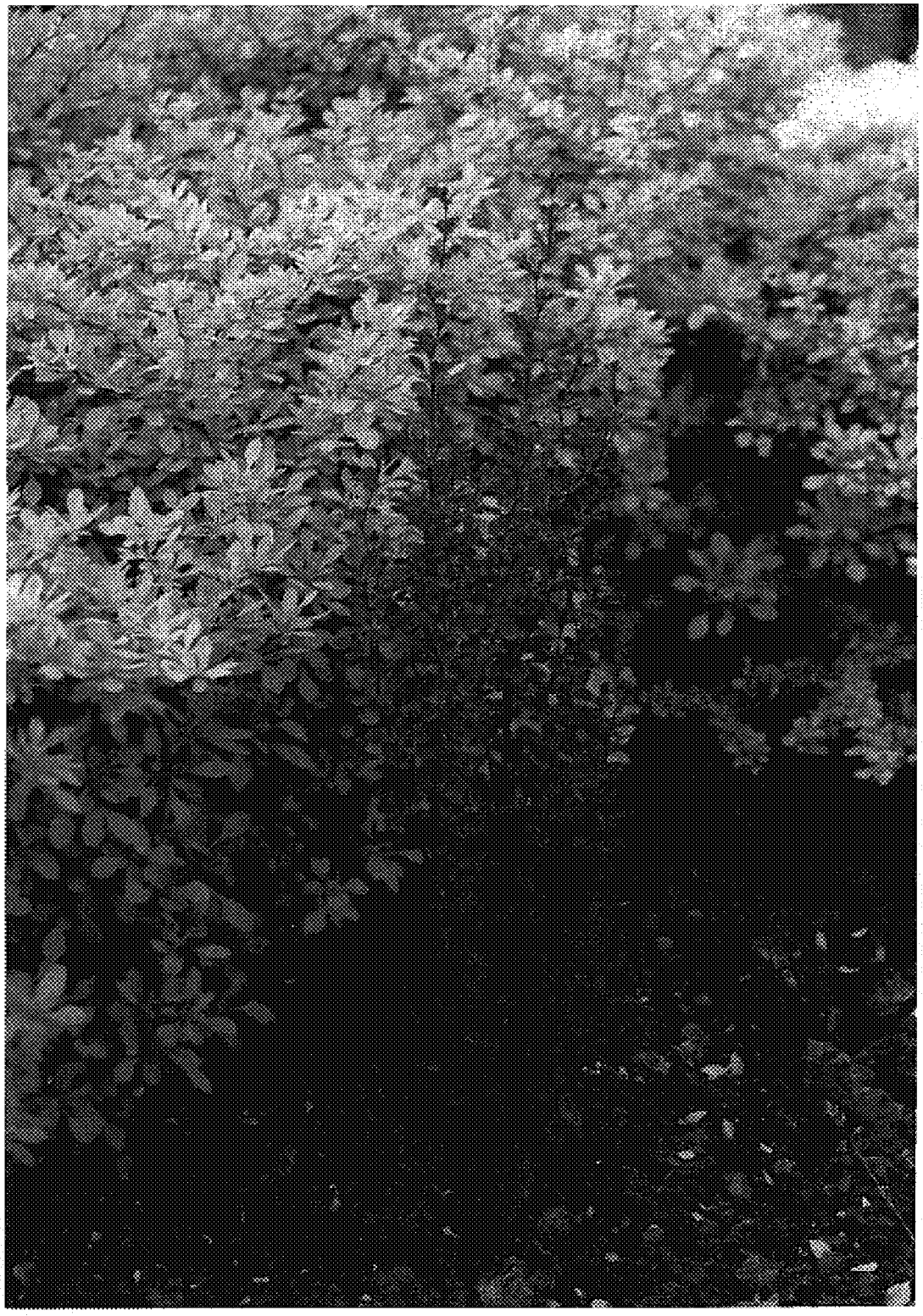

*Berberis* named 'ORANGE ROCKET'. The drawing was made using conventional techniques and although colors may appear different from actual colors due to light reflectance they are as accurate as possible by conventional photography.

BOTANICAL DESCRIPTION OF THE PLANT

The following is a detailed description of 'ORANGE ROCKET' as grown in a 2-liter containers, out-of-doors in Boskoop, The Netherlands. The color determinations are in accordance with the 2001 Edition of the Colour Chart of The Royal Horticultural Society except where general color terms of ordinary dictionary significance are used. The growing requirements are similar to the species.

Botanical classification:
- *Genus.*—Berberis.
- *Species.*—thunbergii.
- *Denomination.*—'ORANGE ROCKET'.

Commercial classification: Deciduous shrub.

Use: Plant for use in containers or landscape.

Common name: Barberry.

Commercial container size: For liner production, a 5 cm round or square plug or cell or container; for planting in the garden or landscape, a 1 gallon or equivalent or larger container.

Cultural requirements: Plant in full sun to light shade in well-drained soil with moderate to regular water.

Parentage: *Berberis* 'ORANGE ROCKET' is a hybrid plant that resulted from cross-pollination of the following parents:
- *Seed parent.—Berberis thunbergii* 'Aurea'.
- *Pollen parent.—Berberis thunbergii* 'Helmond Pillar'.

Plant description:
- *Bloom period.*—Beginning in spring.
- *Plant habit.*—Upright habit.
- *Overall plant shape.*—Columnar.
- *Vigor.*—Low.
- *Root system.*—Fibrous roots.
- *Plant dimensions.*—120 cm in height and 40 cm in width after 10 years.
- *Growth rate.*—Height increases by approximately 15 cm per year.
- *Hardiness.*—USDA Zone 4.
- *Propagation.*—Propagation is accomplished using stem tip or internodal cuttings.
- *Rooting time.*—An average of 6 weeks is needed for an initial cutting to develop roots.
- *Crop time.*—24 months are needed to produce a commercial 2-liter container from a rooted cutting.
- *Special growing considerations.*—Pinching back improves basal branching without losing the columnar habit.
- *Disease resistance and susceptibility.*—Not more susceptible to pests and diseases than other *Berberis thunbergii* cultivars known to the inventor. United States Department of Agriculture, Agricultural Research Service Cereal Disease Laboratory completed testing and found the cultivar resistant to Wheat Stem Rust.

Stem:
- *Dimensions, main stem.*—30 cm in length and 2 mm in diameter.
- *Dimensions, secondary stem.*—29 mm to 40 mm in length and 1.5 mm in diameter.
- *Color, new growth.*—167C to N167C.
- *Color, semi-mature growth.*—172A and 172B.
- *Color, mature growth.*—A mixture of 187A and 201A to 201D.
- *Surface.*—Rough.
- *Spines.*—Present.
- *Spine dimensions.*—7 mm in length.
- *Spine color.*—200B.
- *Spine arrangement.*—Singly and alternate.
- *Spine angle.*—90° on stem.

Foliage:
- *Type.*—Deciduous.
- *Arrangement.*—Borne in alternate clusters of 2 to 4.
- *Leaf division.*—Simple.
- *Leaf shape.*—Obovate to spatulate.
- *Dimensions.*—25 mm to 30 mm in length to 12 mm to 16 mm in diameter.
- *Leaf apex.*—Obtuse to mucronate.
- *Leaf base.*—Attenuate.
- *Leaf venation pattern.*—One-veined from base.
- *Leaf margin type.*—Entire.
- *Leaf surface (adaxial and abaxial).*—Glabrous.
- *Color immature leaf (adaxial).*—181A mottled with 162A.
- *Color immature leaf (abaxial).*—182C and 182D.
- *Color mature leaf (adaxial).*—181A mottled with 162A.
- *Color mature leaf (abaxial).*—182C and 182D.
- *Attachment.*—Some sessile, some petiolate.
- *Petiole length.*—Where petiolate, length varies between 1 mm and 8 mm.

Flowers:
- *Inflorescence form.*—Axillary raceme, 2–4 flowers per raceme.
- *Number per stem.*—10–20 racemes per stem.
- *Time and duration of flowering.*—April — June.
- *Pedicel length.*—12 mm.
- *Dimensions.*—1 cm to 2 cm in diameter, 6 mm to 12 mm in depth.
- *Color.*—4C and 4D.
- *Fragrance.*—None.

Fruit: Borne singly or in clusters of 2–4 fruits at each node.
- *Number per stem.*—30–50.
- *Dimensions.*—1 cm–2 cm.
- *Cover.*—Fleshy.
- *Shape.*—Ellipsoid.
- *Firmness.*—Solid, juicy.
- *Color.*—43A, but brighter, Seeds:
- *Quantity.*—1 or 2 per fruit.
- *Observed immature.*—Green, ellipsoid, 3 mm×2 mm.
- *Not observed mature but may be typical of species.*—Brown, concavo-convex, 3 mm×2 mm.

It is claimed:

1. A new and distinct cultivar of *Berberis* plant named 'ORANGE ROCKET', as described and illustrated here within.

* * * * *